United States Patent [19]

Brown et al.

[11] Patent Number: 4,950,255

[45] Date of Patent: Aug. 21, 1990

[54] CATHETER CONNECTOR AND CLAMP

[75] Inventors: Eric W. Brown, Newport Beach; Charles Kienholz, San Dimas; Earl F. Robinson, El Toro; Rex O. Bare, Irvine, all of Calif.

[73] Assignee: I-Flow Corporation, Irvine, Calif.

[21] Appl. No.: 178,673

[22] Filed: Apr. 7, 1988

[51] Int. Cl.⁵ .............................................. A61M 39/00
[52] U.S. Cl. ...................................... 604/250; 604/283
[58] Field of Search ................................. 604/43–45, 604/51–53, 173, 175, 241–243, 244–250, 280, 283, 256, 103, 257–258; 285/137.1

[56] References Cited

U.S. PATENT DOCUMENTS

| 3,747,632 | 7/1973 | Kok et al. |
| 4,187,846 | 2/1980 | Lolachi et al. |
| 4,257,416 | 3/1981 | Prager ............................ 604/250 X |
| 4,367,740 | 1/1983 | Evanoski . |
| 4,425,113 | 1/1984 | Bilstad ............................ 604/250 X |
| 4,429,852 | 2/1984 | Tersteegen et al. ............. 604/283 X |
| 4,581,012 | 4/1986 | Brown et al. . |
| 4,616,802 | 10/1986 | Tseng et al. .................... 604/250 X |
| 4,695,273 | 9/1987 | Brown ............................ 604/283 X |
| 4,701,159 | 10/1987 | Brown et al. ................... 604/283 X |

FOREIGN PATENT DOCUMENTS 0830081  2/1982  Switzerland .

Primary Examiner—Angela D. Sykes
Attorney, Agent, or Firm—Robert M. Asher

[57] ABSTRACT

A combination catheter connector and clamp provided with an interlocking hook and post for locking two connector parts together. A manifold separates the lumens of a multilumen catheter into separate arms which can be closed or opened by a pushbutton clamp. A silicone block is used between the engagement portions of the connector parts.

23 Claims, 2 Drawing Sheets

CATHETER CONNECTOR AND CLAMP

BACKGROUND OF THE INVENTION

This invention relates to a combination catheter connector and clamp, in particular, one for use with multilumen catheters It has been found convenient for patients who are receiving frequent infusions to provide them with a tunneled subcutaneous catheter. Such a catheter is inserted underneath the skin of the patient and then into a vein. A tissue cuff is provided on the catheter near the skin so that the skin may grow into it and hold the catheter in place. A connector part is located on the end of the catheter above the skin into which a mating connector part may be attached to connect the subcutaneously tunneled catheter with an external catheter. The external catheter may be used for infusion of fluids or for extraction of body fluid for testing A separate catheter clamp may be used in conjunction with such a catheter arrangement so as to permit closing off of the passageway through the catheter.

More recently, there has been an introduction of the use of multilumen catheters in subcutaneously tunneled catheter sets. For example, U.S. Pat. No. 4,581,012 discloses a multilumen locking connector for use in a subcutaneously tunneled catheter set. Clamping of such a multilumen catheter is difficult especially if repeated clamping is desired. A multilumen catheter has walls on its interior separating the plurality of lumens. These interior walls make it difficult to completely clamp off a multilumen catheter and the walls are further subject to being crushed or deteriorated from repeated clamping. It is one object of the present invention to provide a clamp for use in a multilumen catheter set.

SUMMARY OF THE INVENTION

The present invention is directed to a catheter connector including a first lock adapter for mating with a second lock adapter. A post extends from one adapter and a hook is attached to the other adapter so that when the hook engages the post, the two adapters become locked together.

In accordance with a feature of the present invention, the connector may be provided with a clamp for closing off the conduits through one of the adapters. The clamp can be conveniently formed by a push button which rides in a couple of slots in one of the lock adapters By providing a clamp in the connector, the present invention advantageously eliminates the need for separate clamps or a single clamp which may damage a multilumen catheter. Particularly advantageous is the use of the clamp in the multilumen embodiment of the present invention. The clamp is used to shut off the conduits within one of the lock adapters In this manner, no stress is exerted upon the interior walls of a multilumen catheter.

A further advantage of the present invention is that it may be provided with a self-sealing septum which gives the implanted catheter a closed system having no exposure to the air. The septum is penetrated by a needle for providing communication between an external catheter and the implanted catheter.

Other objects and advantages of the present invention will become apparent during the following description of the presently preferred embodiments of the invention taken in conjunction with the drawings.

DETAILED DESCRIPTION OF THE PREFERRED EMBODIMENTS

Figure 1:
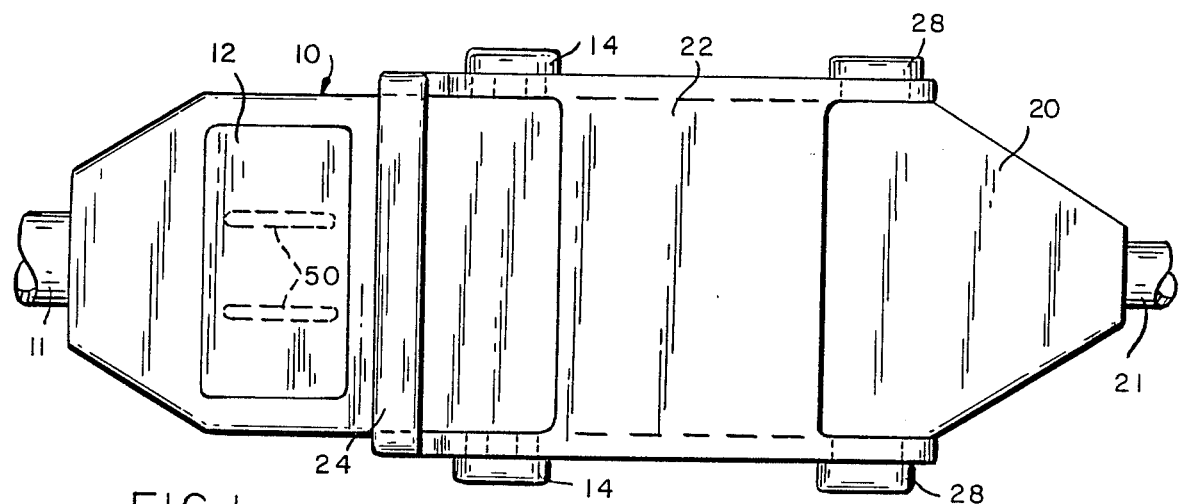
FIG. 1 is a plan view of the combination catheter connector and clamp of the present invention.
Figure 2:
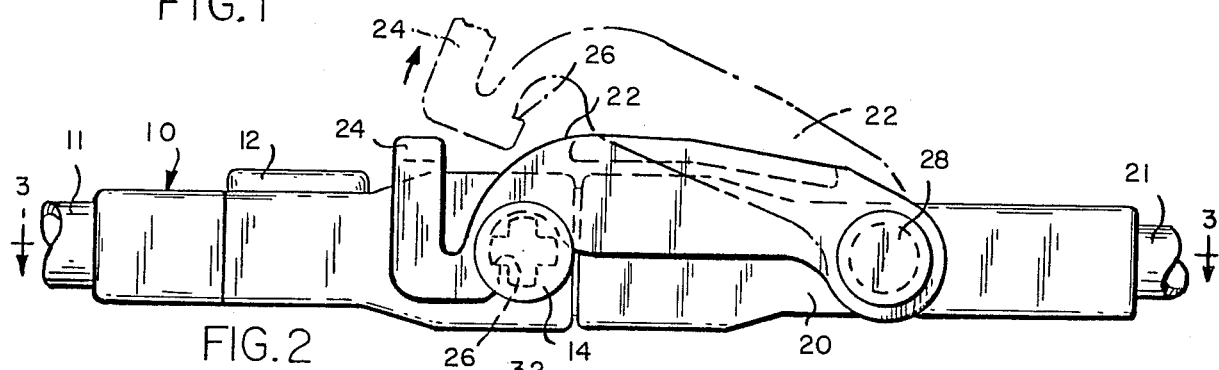
FIG. 2 is an elevational view of the combination catheter connector and clamp of FIG. 1.

Referring now to FIGS. 1 and 2, the combination catheter connector and clamp is shown. A patient connector part 10 is lock adapter attached to a catheter 11 which has been implanted in a patient. A pushbutton clamp 12 is provided in the patient connector part 10 The patient connector part 10 includes conduits providing communication with the lumen or lumens in the implanted catheter 11. The pushbutton clamp 12 is used to close off the conduit or conduits within the patient connector part 10 so as to close off the implanted catheter 11. The patient connector part 10 further includes a locking post 14 which is used when the patient connector part 10 is locked onto a lock adapter referred to herein as the drug connector part 20. The drug connector part 20 is attached to an external catheter 21. The external catheter 21 could be used in connection with an infusion pump for infusing fluid into a patient through the implanted catheter.

The drug connector part 20 carries an interlock 22 which has a handle 24 and a hook 26. The interlock 22 is rotatably connected to the connector 20 about shafts 28. The interlock 22 is shown in solid lines in the locked position with the hook 26 engaging the locking posts 14 of the patient connector 10. The locking posts 14 may be made in the shape of a cross or other equivalent shape to form a ledge that positively engages the hook 26. In the locked position, the lumens of the implanted catheter 11 are in communication through the connector with the lumens of the external catheter 21. The connector can be unlocked by squeezing the connector parts together and pulling up on the handle 24 which causes the interlock 22 to swing about the axis formed by the shafts 28 thereby disengaging the hook 26 from the posts 14. The interlock 22 is drawn in dashed lines to show it in an unlocked position.

Figure 3:
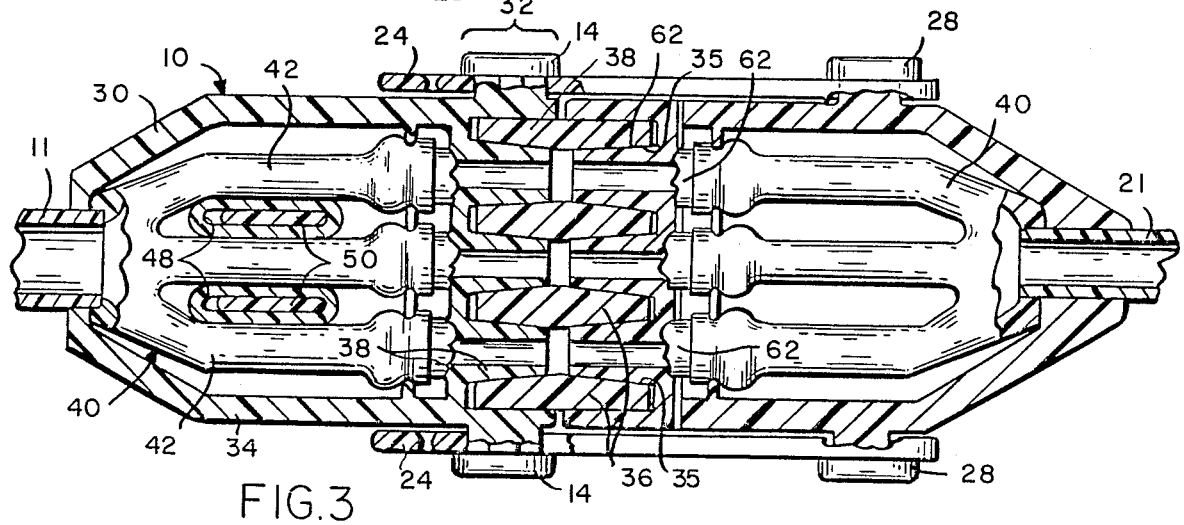
FIG. 3 is a plan view in partial cross-section of the combination catheter connector and clamp of FIG. 1.
Figure 4:
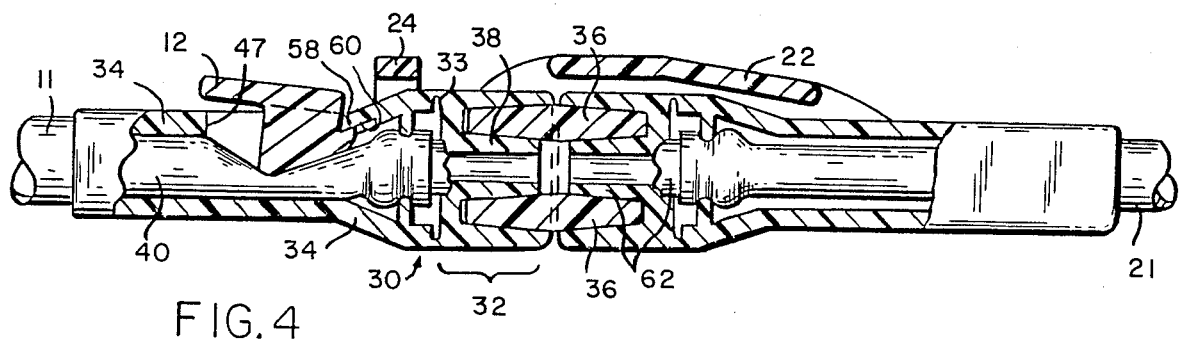
FIG. 4 is an elevational view in partial cross-section of the multilumen catheter connector and clamp of FIG. 1.

The patient connector 10 is described in more detail with reference to FIGS. 3 and 4. A plastic housing 30 includes an engagement portion 32 top and bottom manifold covers 34 and a hinge portions 33 connecting the manifold covers to the engagement portion 32. The engagement portion 32 provides solid conduit tubes 38 for each conduit provided by the connector. A connector is chosen for a catheter so that there is one conduit for each lumen in the catheter. In accordance with the preferred embodiment, a resilient sealing block 36 provides the engagement ports 35 for the patient connector part 10. The sealing block 36, preferably made from silicone, is solid except for a conduit for each of the conduits in the connector. The conduits fit over the solid conduit tubes 38 projecting from the engagement portion 32 of the housing 30. Rather than using the hard plastic conduit tubes as engagement ports, the silicone block is used since it is resilient and can therefore accomodate slight manufacturing variations in the formation of the plastic connector parts or deviations created by handling and use of the plastic connector parts. In this manner, it is easier to ensure that two connector parts can be mated.

On the inside of the housing 30, a manifold 40 is placed for providing fluid communication between the conduit tubes 38 and the lumens of the catheter connected to the connector. The extruded catheter tube is molded to the manifold 40 so that each lumen is separately directed through an independent conduit. Each conduit branches off into one of the plurality of arms 42 on the manifold 40. The manifold 40 and its arms 42 are made of a compressible and resilient material such as silicone so as to properly respond to the action of the clamp 12 Silicone is also preferable because of its known compatibility to various drugs and body tissues. Each arm 42 of the manifold 40 fits over the rear of a conduit tube 38 to provide a separate and distinct conduit for each lumen of the catheter from the junction between the catheter and the manifold 40 through to the engagement ports formed by the silicone block 36.

Figure 6:
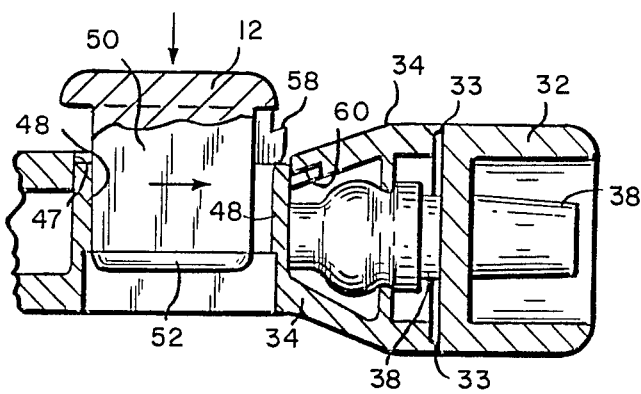
FIG. 6 is a cross-sectional view of the patient connector part of the present invention.
Figure 7:
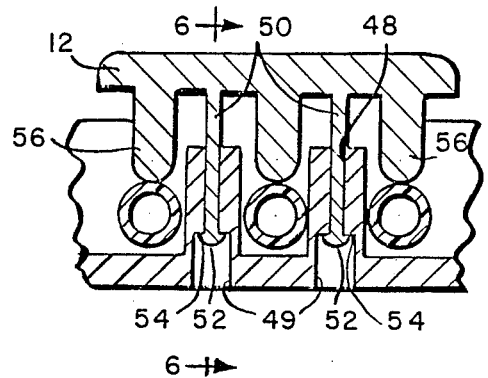
FIG. 7 is a cross-sectional view of the patient connector part of FIG. 6 with the clamp in the open position.
Figure 8:
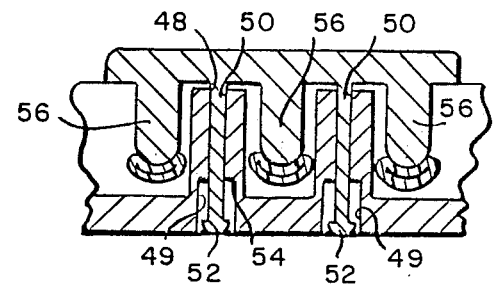
FIG. 8 is a cross-sectional view of the patient connector part of FIG. 6 with the clamp in the closed position.

The top manifold cover 34 has a hole 47 through which the pushbutton clamp 12 fits. The bottom manifold cover 34 is provided with two slots 48 within which the pushbutton clamp 12 rides. Referring now to FIGS. 6–8, the pushbutton clamp 12 includes two guide members 50 which ride up and down in the slots 48. The guide members 50, each includes a restraint portion 52 at its end. The restraint portion is expanded with respect to the guide member in order to prevent the pushbutton 12 from coming out of the slots 48 The restraint portion may be formed in the mold for the push button clamp or alternatively the bottoms of the guide members can be heat staked to form the restraint portions after the molding process. The restraint portions 52 ride within a widened portion 49 of the slots. The restraint portions 52 hit up against a shoulder 54 where the widened portion 49 meets the narrow portion of the slots 48. This action as shown in FIGS. 6 and 7 keeps the clamp 12 secured onto the connector.

In manufacture of this connector, the top and bottom manifold covers 34 are swung open along the hinge portions 33. The manifold 40 molded to the patient catheter is attached to the rear of the conduit tubes 38. The top and bottom manifold covers 34 are then swung closed so as to envelope the manifold. The pushbutton clamp 12 is then inserted through the top manifold cover 34 into the slots 48. The restraint portions 52 of the clamp are forced through the narrow portion of the slots 48 until they snap into the widened portion 49. The silicone block 36 is then force fit onto the tubes 38.

The pushbutton clamp 12 further includes a flow restrictor member 56 for each of the arms 42 of the manifold. The flow restrictor members 56 are shorter than the guide members 50 so that when the button 12 is up as in FIGS. 6 and 7 the flow restrictor members 56 do not cause any restriction in the flow of fluids through the arms 42 of the manifold. The flow restrictor members 56 of the preferred embodiment are provided with a clamping ledge 58 which is provided for sliding under a restraining wall portion 60 of the upper manifold cover 34. Thus to effect clamping, the pushbutton 12 is pushed down and forward into the position shown in FIG. 4 so that the clamping ledge 58 engages the wall portion 60. In this position, the flow restrictor members 56 are held down against the arms 42 of the manifold 40 so as to close off the conduits there within as shown in FIG. 8. While the back of the clamp 12 may bow up off the connector housing, the parts are dimensioned to ensure complete closure of the conduits when the clamp is in the closed position.

The drug connector part 20 is now discussed in more detail. As in the patient connector part 10, the drug connector part 20 includes a silicone manifold 40 in this case molded to the external catheter 21. The manifold may be made of silicone or a medical-grade plastic, such as PVC. The arms of the silicone manifold 40 plug onto the interior projections of conduit tubes 62. The outer ends of conduit tubes 62 form the engagement ports for the drug connector part 20. These engagement ports fit into the conduits of the silicone block 36 carried by the patient connector part 10. Thus, the drug connector part provides a conduit for each of the lumens in the external catheter from the catheter through to the engagement ports at the outer ends of the conduit tubes 62. The resiliency of the silicone block 36 permits the engagement portion of the drug connector part 20 to fit over the block and the tube projections to fit into the conduits despite any minor manufacturing tolerances in the formation of the drug connector part. When the engagement ports of the connector parts are fully inserted into the silicone block, the interlock 22 can be brought down into place so that the hook 26 engages the post 14 of the patient connector. A slight compression of the silicone block occurs to ensure a good seal.

Figure 5:
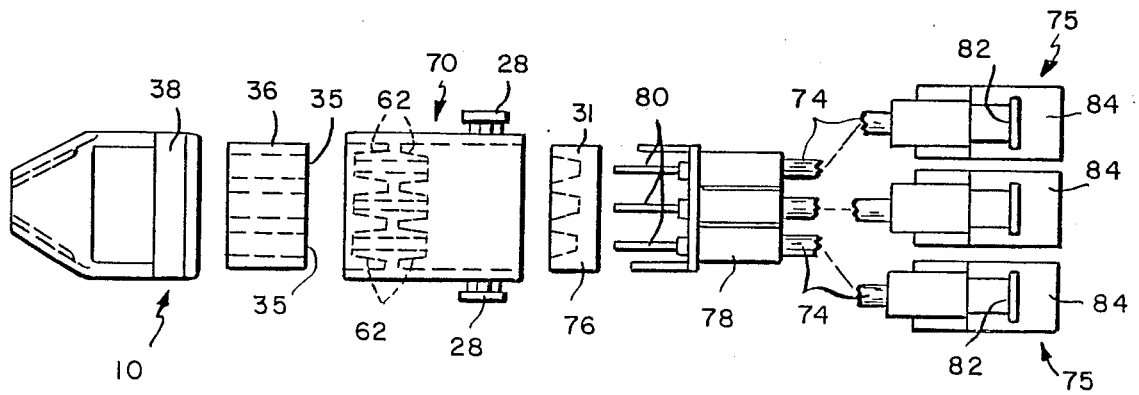
FIG. 5 is an exploded view of an alternate embodiment of the combination catheter connector and clamp of the present invention.

In accordance with an alternate embodiment of the present invention, rather than providing a drug connector part connected to a multilumen catheter, an injection connector part 70 may be used for interacting with a needle holder 78 as shown in FIG. 5. The needle holder 78 may be provided with single lumen lines 74 connected to injection ports 75 permitting the use of a syringe to repeatedly inject a drug solution through an injection port and into any one of the lumens of the patient catheter. The injection connector part 70 has a housing which surround conduit tubes 62. The conduit tubes 62 form the engagement ports at their outer ends as in the drug connector part. A silicone self-sealing septum 76 is provided for insertion into the rear of the housing 70 so that the rear of the conduit tubes 62 fit into matching holes in the septum 76. An interlock 22, not shown, is rotatably attached to the connector part housing at shafts 28. Thus, the injection connector part may be plugged into the patient connector part and locked thereto by the interlock 22. This will provide a closed system for the patient The self-sealing septum 76 will prevent air from entering the conduits which lead into the patient's multilumen catheter.

The needle holder 78 is provided with needles 80 aligned for insertion through the septum 76 and into the conduit tubes 62. When the septum 76 is penetrated by the needles, the needles extend through the septum to provide communication between the conduit tubes 62 and the single lumen lines 74 at the rear of the needles 80. Each needle 80 has a single lumen line 74 in communication therewith. The single lumen lines 74 are attached to the rear of the needle holder 78. At the other end of each catheter is a luer connector 82 which is provided with its own self-sealing septum 84. The septum 84 and luer connectors 82 form the injection ports 75. Injections may be made by a syringe needle through the self-sealing septum 84 of one of the single lumen lines connected at the rear of the needle holder 78. This permits selective injection of fluids into the individual lumens of an implanted multilumen catheter.

Of course, it should be understood that various changes and modifications to the preferred embodiments described above will be apparent to those skilled in the art. For example, a spring biased clamp may be used to replace the pushbutton clamp on the patient connector part. This and other changes can be made without departing from the spirit and scope of the invention and without diminishing its attendant advantages. It is therefore intended that such changes and modifications be covered by the following claims.

We claim:

1. A multilumen connector part comprising:
   a housing having a plurality of engagement parts at one end and means for receiving a multilumen catheter at an other end;
   a manifold having a plurality of compressible and resilient conduits within said housing, said manifold providing independent fluid communication between each lumen of said multilumen catheter and a different one of said conduits and said conduits each leading to a different one of said plurality of engagement ports; and
   clamping means attached to said housing for selectively closing off said plurality of conduits by pushing against all of said conduits in an area of said housing where said conduits are arranged in a non-overlapping manner.

2. The multilumen connector part of claim 1 wherein said clamping means comprises a pushbutton having flow restrictor members which close off said plurality of conduits when said pushbutton is held in a closed position.

3. The multilumen connector part of claim 2 wherein said pushbutton further includes guide members for riding up and down in slots formed in said housing.

4. The multilumen connector part of claim 2 wherein said pushbutton further includes a ledge engaging said housing to hold said pushbutton against said housing when said pushbutton is in a closed position.

5. The multilumen connector part of claim 1 further comprising post means extending from said housing so as to be available for making locking engagement with a second multilumen connector part.

6. The multilumen connector part of claim 1 further comprising a resilient sealing block secured within said housing for forming the engagement ports.

7. A catheter connector comprising:
   a first lock adapter including means for receiving a catheter having at least one lumen, an engagement port for each lumen and a conduit for each port connecting said port to one of said at least one lumen;
   a second lock adapter having an engagement portion connectable to said first lock adapter so that each said conduit in said first lock adapter interconnects with a conduit in said second lock adapter;
   post means extending out from one of said first or second lock adapters; and
   hook means attached to the other of said first or second lock adapters so that said first lock adapter is locked to said second lock adapter when said hook means engages said post means.

8. The catheter connector of claim 7 further comprising clamp means attached to said first lock adapter for selectively closing each said conduit in said first lock adapter.

9. The catheter connector of claim 8 wherein said clamp means comprises a pushbutton attached to said housing and flow restrictor members extending from said pushbutton for closing off said conduits when said pushbutton is in a closed position.

10. The catheter connector of claim 9 wherein said pushbutton further includes guide members which fit through slots formed in said housing, said guide members having expanded portions at their ends for preventing said guide members from coming out of the slots thereby maintaining said pushbutton attached to said housing.

11. The catheter connector of claim 7 wherein said hook means comprises a member having a hook at one end and a rotatable attachment at an other end.

12. The catheter connector of claim 7 wherein said second lock adapter further includes a penetrable self-sealing septum covering each conduit in said second lock adapter.

13. The catheter connector of claim 12 further comprising a needle holder having a needle for each conduit in said second lock adapter, each needle being insertable through said septum so as to be put in communication with a conduit in said second lock adapter.

14. The catheter connector of claim 7 further comprising a resilient sealing block for connecting the engagement portion of said second lock adapter to the engagement ports of said first lock adapter.

15. A catheter connector part comprising:
   a housing having means for receiving a catheter having at least one lumen, an engagement port for each lumen and a conduit for each port connecting said port to one of said at least one lumen;
   post means extending from said housing so as to be available for making locking engagement with a second catheter connector part;
   a pushbutton attached to said housing; and
   flow restrictor members extending from said pushbutton for closing off said conduits when said pushbutton is in a closed position.

16. The catheter connector part of claim 15 wherein said pushbutton further includes a ledge for engaging said housing to hold said pushbutton in the closed position.

17. The catheter connector part of claim 15 wherein said pushbutton includes guide members which fit through slots formed in said housing, said guide members having expanded portions at their ends for preventing said guide members from coming out of the slots thereby maintaining said pushbutton attached to said housing.

18. The catheter connector part of claim 15 further comprising a resilient sealing block for connecting the engagement ports of said housing with the engagement portion of a second catheter connector port.

19. A catheter connector part comprising:
   a housing having means for receiving a catheter having at least one lumen, an engagement port for each lumen and a conduit for each port connecting said port to one of said at least one lumen;
   hook means for making locking engagement with a second multilumen connector part;

a pushbutton attached to said housing; and flow restrictor members extending from said pushbutton for closing off said conduits when said pushbutton is in a closed position.

20. The catheter connector part of claim 19 wherein said hook means comprises a member having a hook at one end and being rotatably attached to said housing at an other end.

21. The catheter connector part of claim 20 wherein said pushbutton includes guide members which fit through slots formed in said housing, said guide members having expanded portions at their ends for preventing said guide members from coming out of the slots thereby maintaining said pushbutton attached to said housing.

22. The catheter connector part of claim 20 further comprising a resilient sealing block for connecting the engagement ports of said housing with the engagement portion of a second catheter connector port.

23. The catheter connector part of claim 22 wherein said pushbutton further includes a ledge for engaging said housing to hold said pushbutton in the closed position.

* * * * *